(12) United States Patent
Jones

(10) Patent No.: US 11,013,586 B2
(45) Date of Patent: *May 25, 2021

(54) DENTAL TESTING DEVICE FOR HEAT SENSITIVITY

(71) Applicant: Thomas L. Jones, Ashville, NC (US)

(72) Inventor: Thomas L. Jones, Ashville, NC (US)

( * ) Notice: Subject to any disclaimer, the term of this patent is extended or adjusted under 35 U.S.C. 154(b) by 246 days.

This patent is subject to a terminal disclaimer.

(21) Appl. No.: 16/169,484

(22) Filed: Oct. 24, 2018

(65) Prior Publication Data

US 2019/0117359 A1    Apr. 25, 2019

Related U.S. Application Data

(63) Continuation of application No. 12/611,396, filed on Nov. 3, 2009, now Pat. No. 10,136,977.

(60) Provisional application No. 61/198,249, filed on Nov. 3, 2008.

(51) Int. Cl.
*A61C 19/04* (2006.01)
*A61B 5/00* (2006.01)
*A61C 17/22* (2006.01)

(52) U.S. Cl.
CPC ............ *A61C 19/04* (2013.01); *A61B 5/4824* (2013.01); *A61C 17/224* (2013.01)

(58) Field of Classification Search
CPC ..... A61C 19/04; A61C 17/224; A61B 5/4824; A61B 5/0534; A61B 5/4547; A61B 5/483; A61B 18/082; A61B 18/08

USPC .......................................................... 433/32
See application file for complete search history.

(56) References Cited

U.S. PATENT DOCUMENTS

| | | |
|---|---|---|
| 439,238 A | 10/1890 | Faught |
| 2,949,107 A | 8/1960 | Ziegler |
| 3,128,759 A | 4/1964 | Bellis |
| 3,274,995 A | 9/1966 | Eidus |
| 3,618,590 A | 11/1971 | Frank et al. |
| 3,782,366 A | 1/1974 | Brown |
| 3,841,311 A | 10/1974 | Brown |
| 4,164,214 A | 8/1979 | Stark et al. |
| 4,177,799 A | 12/1979 | Masreliez |
| 4,215,698 A | 8/1980 | Nuwayser |
| 4,308,013 A | 12/1981 | Major |
| 4,350,488 A | 9/1982 | Davis |
| 4,527,560 A | 7/1985 | Masreliez |
| 4,759,712 A | 7/1988 | Demand |
| 4,763,657 A | 8/1988 | Chen et al. |
| 4,859,182 A | 8/1989 | Nerli |
| 4,993,946 A | 2/1991 | Kirsch |
| 5,797,744 A | 8/1998 | Rosenberg |
| 10,136,977 B2 * | 11/2018 | Jones ................ A61C 19/04 |
| 2005/0136373 A1 | 6/2005 | Fischer et al. |
| 2006/0074339 A1 | 4/2006 | Adolfsson et al. |

* cited by examiner

*Primary Examiner* — Nicholas D Lucchesi
*Assistant Examiner* — Mirayda A Aponte
(74) *Attorney, Agent, or Firm* — Polsinelli PC

(57) ABSTRACT

A device for testing a heat sensitivity in teeth, a heated cushion for a dental device for testing a heat sensitivity, and a method for testing a tooth for a heat sensitivity.

26 Claims, 9 Drawing Sheets

FIG. 16
FIG. 17
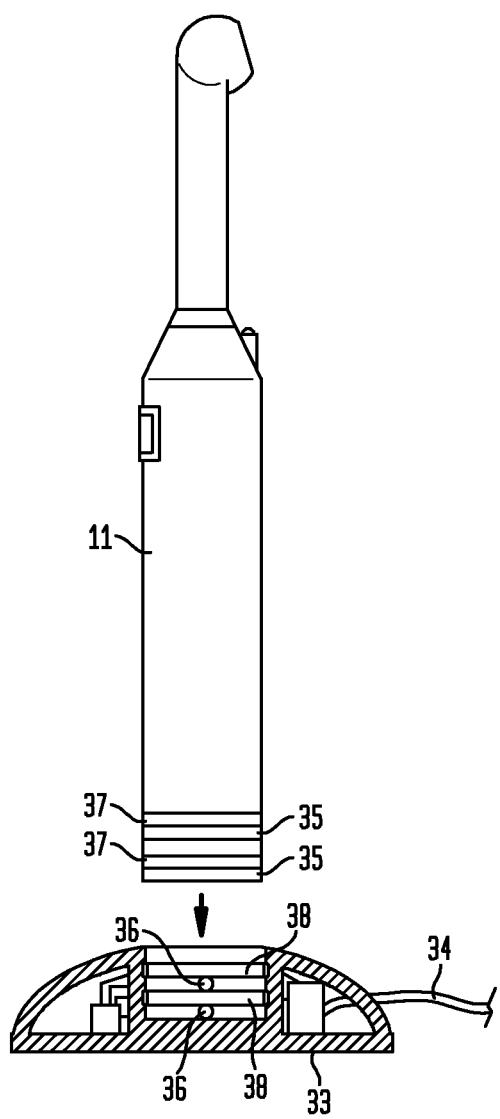
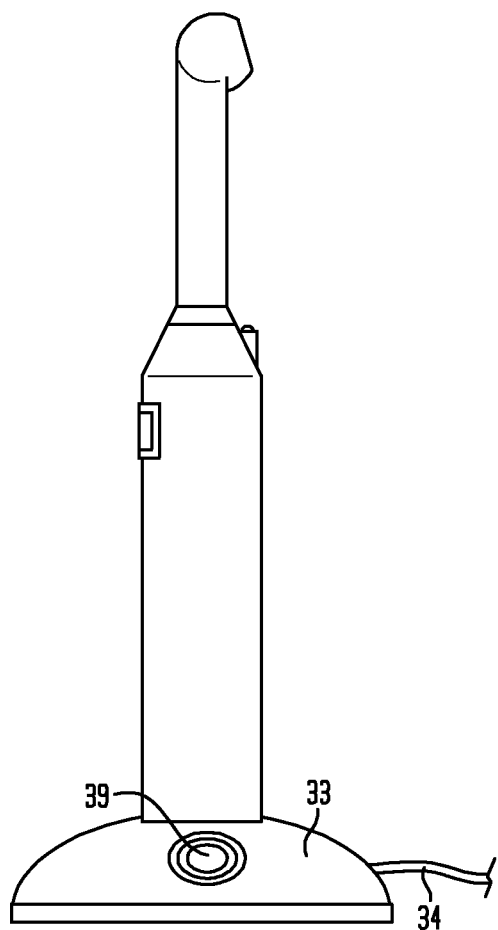

DENTAL TESTING DEVICE FOR HEAT SENSITIVITY

CROSS REFERENCE TO RELATED APPLICATIONS

This application is a Continuation of U.S. application Ser. No. 12/611,396 filed on Nov. 3, 2009, which claims the benefit of priority of U.S. Provisional Patent Application No. 61/198,249, filed on Nov. 3, 2008, the entire contents of which are incorporated herein by reference in their entirety.

TECHNICAL FIELD

The present invention relates generally to a testing device and method for testing and identifying heat sensitivity in teeth.

BACKGROUND

A heat sensitivity in a tooth results in the most intense pain seen by the dental profession. Current methods for diagnosing the tooth from which the pain is emanating are primitive. Presently, a device does not exist for testing for a heat sensitivity in a single tooth. A patient dental history reporting a heat sensitivity in a tooth is important in diagnosing the health of the pulp tissue and the prognosis for recovery. While the patient can report such a sensitivity with relative accuracy, they are most often confused about the tooth in which the sensitivity exist. This confusion is related to how a person attempts to resolve the confusion of dental pain. For instance, if the pain is due to pressure on a tooth, the patient can usually identify the tooth by repeated testing with pressure. If the pain is related to hot or cold, testing involves putting cold or hot liquids, or cold or hot food on the teeth. This testing modality involves a much less precise test than pressing on a single tooth.

Most, if not all of the teeth in a quadrant are subjected to the thermal changes of the test. A patient feels the pain and, in many cases, thinks they know which tooth it is related to, but clinical testing demonstrates that they are incorrect much of the time. This confusion is related to neural anatomy and learning. Little space in the brain is allocated to sensory input from teeth, unlike hands which get a lot of attention and "space" in the brain. From an early age, humans begin to learn to locate where any sensation on their hand is originating from. The ability to visually perceive the area of the hand touching something helps to correlate a sensation with an act. No such relationship exist with teeth.

However, the learning process is the same. Specifically, if a person experiences a dental pain and associate it with a particular tooth your brain will not argue with you. The brain accepts it as a learning experience. If a person experiences the pain again, their brain will identify the tooth they told their brain was causing the pain. The more pain episodes the patient experiences the more reluctant they are to believe the pain could be coming from any other tooth.

A dentist can perform most of the sensitivity testing on single teeth, but a convenient, reliable, safe, method does not exist for testing for a heat sensitivity. Without a convenient, reliable, safe, method for testing for heat sensitivity, the probability of treating the wrong tooth is increased. In particular, much of a dental diagnosis is the dentist's best guess after reviewing the test results. Samples of the suspect tooth cannot be sent to a lab for analysis. That would injure the tooth, irreparably. It is considered unwise for any dentist to treat a heat sensitive tooth unless it can be identified to the patient precisely. Especially, if the patients believes it to be a different tooth. Therefore, a presumed safes action for the dentist may be to do nothing until the tooth becomes sensitive to percussion or bite sensitivity, something more easily demonstrated to the patient. The waiting period usually results in a period of intense pain for the patient; a pain which does not respond well to pain medication.

Therefore, what is needed is a convenient, safe, and reliable, testing device for testing for a heat sensitivity. While other devices have been suggested to have potential utility in testing for a heat sensitivity in teeth, they have no utility in the limited space provided for dental treatment or they disadvantageously have a flat or a rounded metal tip, which cannot conform to the convex tooth surface. Another drawback is that such devices produce a point contact with the convex tooth surface. Heat delivered in this manner must include massive amounts of heat energy to the point contact (considerably in excess of a safe limit that will not cause damage to the enamel, dentin, and the soft tissue of the pulp) to engage the enamel and dentine to become the heat source for testing the pulp tissue for a heat sensitivity. The heat emanating from a point source must be heated to much higher temperatures at the source to compensate for the small surface area conducting the heat.

Thus, in view of the above disadvantages, limits, and drawbacks, the present invention provides a convenient, reliable, and safe testing device for heat sensitivity in teeth. The device enables dentists and other professionals in the field of dentistry to have confidence in identifying a single tooth responsible for a heat sensitivity, which is extremely painful, and treat the tooth most always resulting in immediate relief to the patient.

SUMMARY

In one aspect of the disclosure, a device for testing a heat sensitivity in teeth is disclosed. The testing device comprises: a base; and a tip having a cushion, wherein the cushion comprises a heating element, and wherein the cushion conforms to a contour of a tooth tested for a heat sensitivity.

In another aspect of the disclosure, a cushion for a dental device is disclosed. The cushion comprise: a heating element; wherein the cushion is located on the tip or end of the dental testing device, wherein heat energy is transferred from the cushion to a single tooth tested for a heat sensitivity.

In a further aspect of the disclosure, a method for testing a tooth for a heat sensitivity is disclosed. The method comprises: applying a dental testing device comprising a tip having a cushion to a tooth; heating the cushion; and transferring heat energy from the cushion to the tooth, wherein the cushion conforms to a contour of the tooth.

BRIEF DESCRIPTION OF THE DRAWINGS

FIG. 15 B shows an end view (27) of the same heated cushion.

FIG. 15 C shows a side view of the same heated cushion (2

FIG. 15 D illustrates how the design of the heated cushion would allow it to relate to incisor teeth (29).

FIG. 15 E illustrates how the design of the heated cushion would allow it to relate to canine teeth (30).

FIG. 15 F illustrates how the design of the heated cushion would allow it to relate to bicuspid teeth (31).

FIG. 15 G illustrates how the design of the heated cushion would allow it to relate to and molar teeth (32).

FIG. 16 illustrates the testing device of the present invention having a docking station (33) (illustrated in cross section).

FIG. 17 illustrates the testing device of the present invention resting in the docking station (33).

DETAILED DESCRIPTION OF THE DISCLOSURE

The present disclosure and the various features and advantageous details thereof are explained more fully with reference to the non-limiting embodiments that are illustrated in the accompanying drawings and detailed in the following description.

Figure 1:
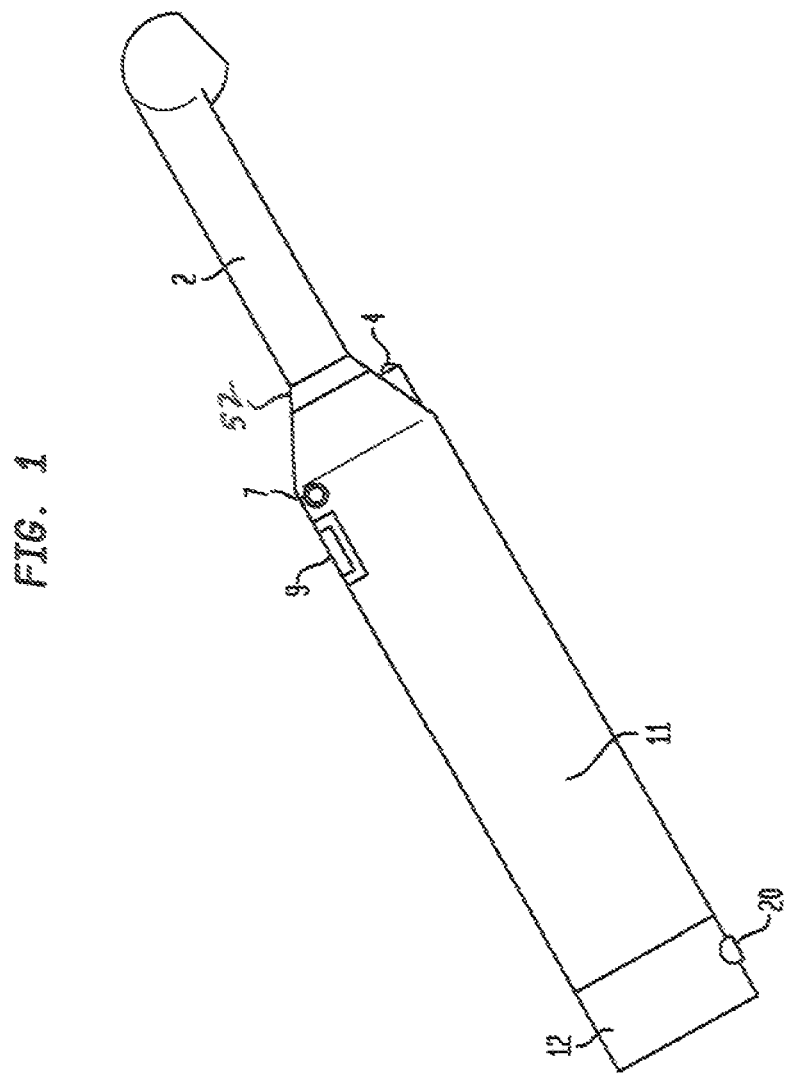
FIG. 1 illustrates a side view of the testing device of the present invention.

FIG. 1 shows a side view of the testing device invention. The tip of the testing device (2) may be removed from the handle (11) of the testing device for the purpose of sterilization of the entire tip. The push button switch (9) turns the device on. A LED light (7) is energized to indicate that the testing device has been activated and that the heating element in the heated cushion located in the tip (2) above the base (52) is energized. A white LED light (4) is activated when the circuit containing a thermistor is energized and the circuit containing the heating element in the heated cushion is no longer energized. The white LED (4) also serves to illuminate the area being tested and aid in the proper placement of the heated cushion located in the tip (2). A screw-type cap (12) is located at the base of the testing device for ease of loading batteries into the cylindrical handle to power the testing device. An electrical jack (20) is located in the base for an alternative energy source and/or to charge rechargeable batteries.

Figure 2:
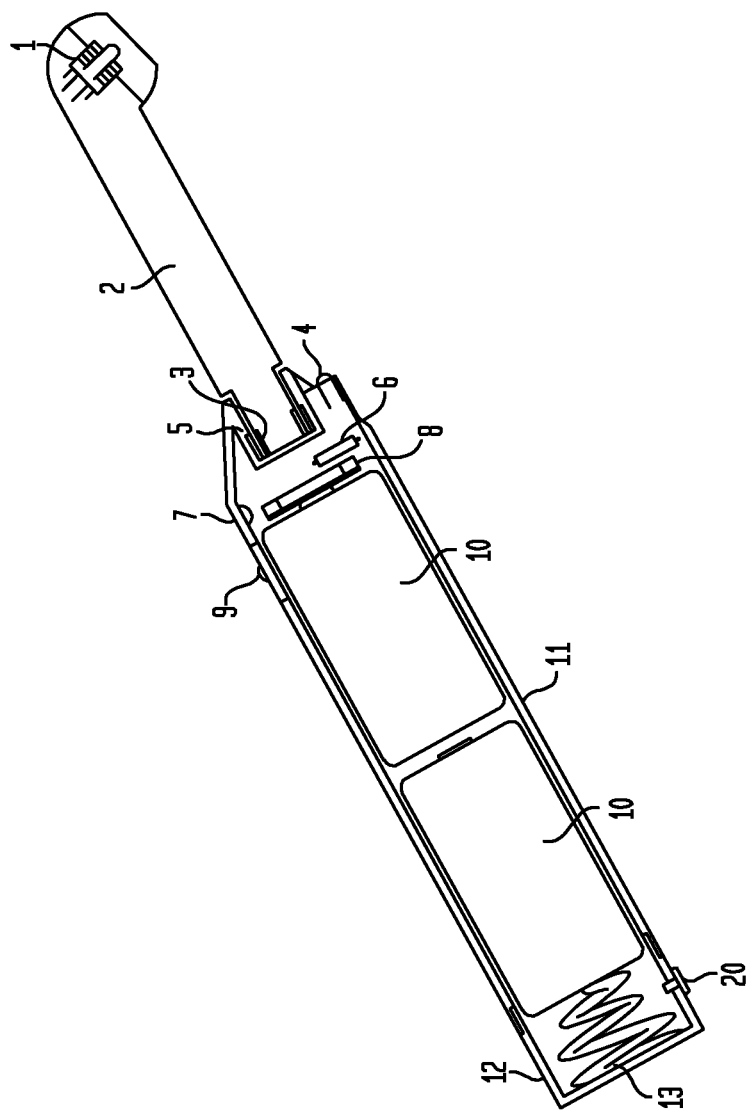
FIG. 2 illustrates a cross section of the testing device invention.

FIG. 2 shows a cross section of the testing device invention. The location of the heated cushion (1) in the tip (2) of the testing device is angled for ease of use and visibility when positioning the cushion on a tooth. The metal contacts (3) at the base of the tip (2) have a complimentary set of metal contacts (5) in the handle (11) of the testing device. Two of the metal contacts (3) in the tip (2) of the testing device are wired to the heating element in the heated cushion (1) in the tip (2) of the testing device. The other two metal contacts (3) are wired to a thermistor in contact with the heated cushion (1) in the tip (2) of the testing device. Complimentary metal contacts in the handle of the testing device (5) connect the circuits of the heating element in the heated cushion (1) and the thermistor to the positive, battery disk (8) and the push button switch (9), which is connected to the metal handle (11) and when closed, will complete the circuit to the negative end of the batteries (10) through the spring (13) in the end-cap (12) of the handle (11). A resistor (6) may be added to either the circuit containing the heating element or the circuit containing the thermistor, to create a greater resistance in the circuit containing the thermistor at the time the switch is closed. An electrical receptacle (20) is located near the base of the testing device to allow an adapter connected to an exterior electrical source to be jacked into the testing device to recharge the batteries (10) or energize the testing device. This heat limiting assembly is illustrated; others using a variety of thermostat mechanisms may be used.

Figure 3:
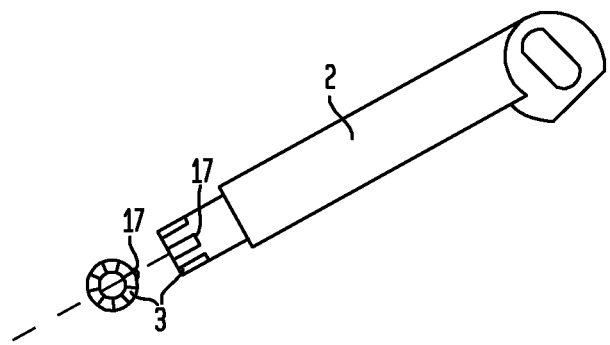
FIG. 3 illustrates the tip (2) which may be removed for sterilization.

FIG. 3 shows the tip (2) which may be removed for sterilization. The metal contacts (3) at the base of the tip (2) are wired to the heating element in the heated cushion and the thermistor in the tip of the testing device. A raised key (17) at the base of the tip (2) inserts into a slot in the handle of the testing device to align the metal contacts (3) on the tip (2) with the proper metal contacts in the handle.

Figure 4:
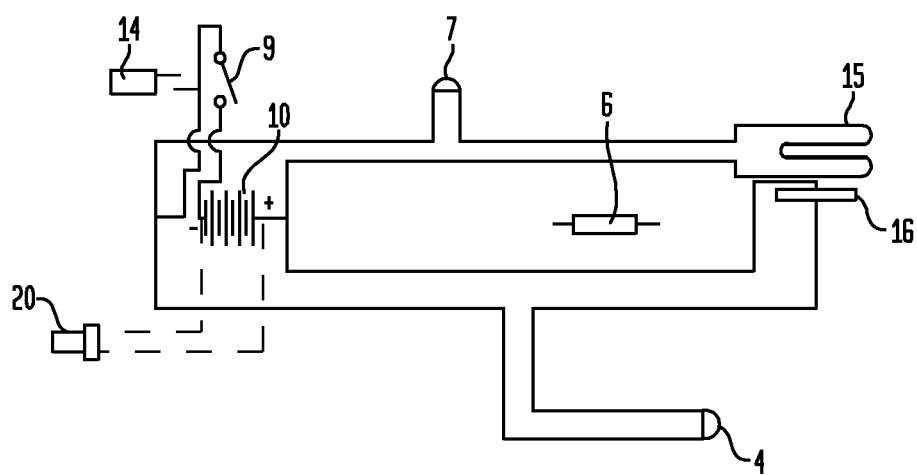
FIG. 4 illustrates the circuitry of the testing device of the present invention.

FIG. 4 shows the circuitry of the testing device invention. One circuit contains the heating element (15) in the heated cushion (1), a blue LED light (7) and possibly a resistor (6). A second circuit contains a thermistor (16), a white LED light (4), and possibly a resistor (6). When the push button switch (9) is closed, electrical energy in the battery source (10) flows through the circuit containing the heating element (15) in the heated cushion in the tip (2) of the testing device and the blue LED (7) is energized signaling to the user that the heating element (15) in the heated cushion is energized. As the heating element (15) heats the area of the heated cushion where the thermistor (16) is located, the resistance in the thermistor (16) is reduced allowing the circuit containing the thermistor (16), which is greater in resistance to the circuit containing the heating element (15), to become activated as the heat lowers the resistance in the thermistor (16) allowing the circuit containing the thermistor (16) to become the path of least resistance diverting electrical energy from the circuit containing the heating element (15) in the heated cushion and limiting the temperature of the heated cushion and energizing the white LED light (4) signaling that the testing device is ready to conduct the test. The lighting provides safety by observing both LED lights, blue (7) and white (4). If both lights are lit the testing device is malfunctioning. If the white LED light (4) is lit, there is no electrical energy in the heating element (15). The testing device should not be used if the blue LED light (7) is lit or the white light (4) and the blue light (7) are both lit. The maximum temperature of the heated cushion (1) is determined by the heat range of the thermistor (16) used. Thermistors are engineered to loose resistance in a temperature range. A timing circuit (14) may be added to the push button switch (9) to conserve power in the event the operator of the testing device forgets to turn it off when he is finished using it. An additional feature of the testing device is an electrical jack (20) which may be added to the circuit to allow for a transformer to utilize household current to energize the testing device and/or recharge the batteries.

Figure 5:
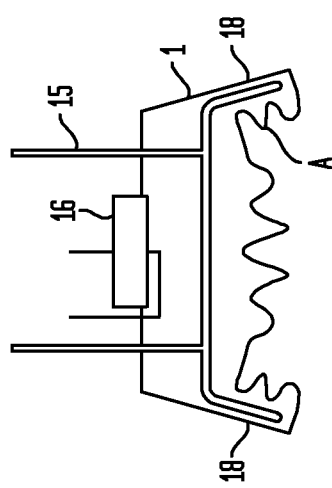
FIG. 5 illustrates an enlarged cross section of the heated cushion (1) of the present invention, illustrating the position of the heating element (15) and a thermistor (16) abutting the heated cushion (1).

FIG. 5 shows an enlarged cross section of the heated cushion (1) illustrating the position of the heating element (15) and a thermistor (16) abutting the heated cushion (1). The heated cushion (1) may be constructed of a heat resistant silicon rubber, or any durable, heat resistant rubber. The heated cushion (1) has a design that allows rubber between grooves in the base of the cushion to deform and contour to the unique contours of different types of teeth, incisors, canines, premolars, and molars. As shown in FIG. 5, the left side of the heated cushion (1) is a mirror image of the right side. This allows the cushion to be used on the right side of the mouth and the left side of the mouth or to test on the buccal side (the side of a tooth touching the lips or cheek) of a tooth or the lingual side (the side of a tooth touching the tongue) of a tooth. The area (A) in the heated cushion (1) allows an incisor edge or the cusp of a tooth to penetrate into the area of the heated cushion (1) allowing the extension (18) of the heated cushion to extend to, and contact the vertical side of the tooth to allow for heat transfer from the heated cushion (1) to the tooth on the vertical side as well as the occlusal surface.

Figure 6:
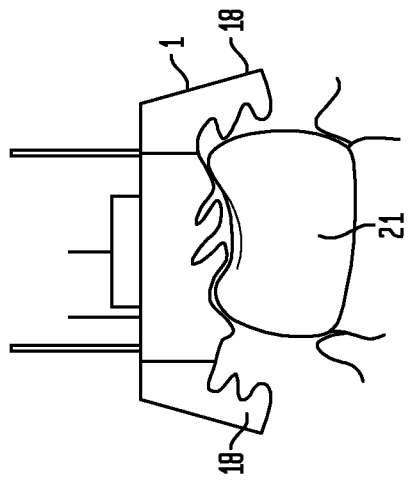
FIG. 6 illustrates how the grooves of the heated cushion (1) of the present invention allow the ridges of the cushion to deform into the space provided by the grooves and contour to the surface of the tooth (21).

FIG. 6 shows how the grooves of the heated cushion (1) allow the ridges of the cushion to deform into the space provided by the grooves and contour to the surface of the tooth (21) placing the maximum surface area of the heated cushion on the surface of the tooth. A softer, more compressible, less dense, may be used that would conform to the tooth surface without grooves and ridges.

Figure 7:
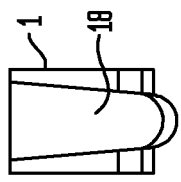
FIG. 7 illustrates an enlarged end view of the heated cushion (1) of the present invention showing the extension (18).

FIG. 7 shows an enlarged end view of the heated cushion (1) showing the extension (18).

Figure 8:
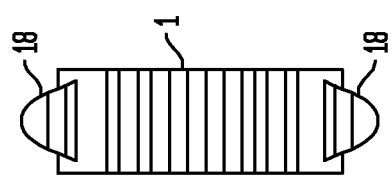
FIG. 8 illustrates an enlarged view of the base of the heated cushion (1) of the present invention.

FIG. 8 shows an enlarged view of the base of the heated cushion (1). The cushion is designed to extend down the vertical surface of a tooth with minimal, or no, contact with the tissue and has a depth that will limit the coverage to a single tooth with no, or minimal contact with adjacent teeth. The heated cushion (1) is wide enough to accommodate the wider molars. The extensions (18) of the heated cushion (1) are illustrated at either end of the heated cushion (1).

Figure 9:
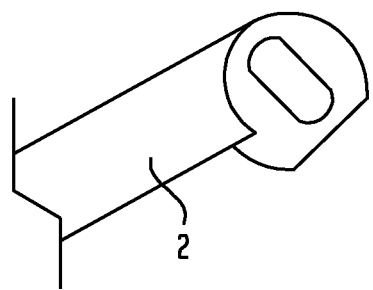
FIG. 9 illustrates the tip of the testing device (2) of the present invention.

FIG. 9 shows the tip of the testing device (2).

Figure 10:
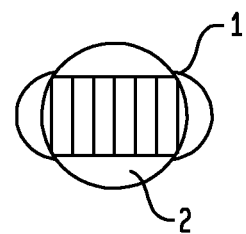
FIG. 10 illustrates a view of the tip of the testing device (2) of the present invention in which the heated cushion (1) can be seen, actual size.

FIG. 10 shows a view of the tip of the testing device (2) in which the heated cushion (1) is shown.

Figure 11:
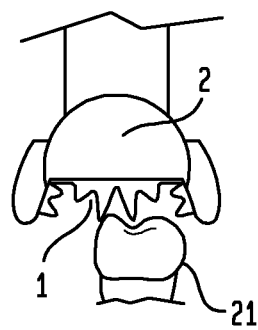
FIG. 11 illustrates the tip of the testing device (2) of the present invention with the heated cushion (1) enclosed; as it relates to an averaged sized molar (21).

FIG. 11 shows the tip of the testing device (2) with the heated cushion (1) enclosed; as it relates to an averaged sized molar (21).

Figure 12:
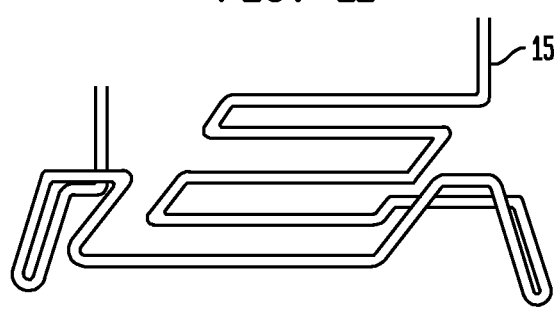
FIG. 12 illustrates the configuration of a heating element of the type (15) embedded in the heated cushion (1) of the present invention.

FIG. 12 shows the configuration of a heating element of the type (15) embedded in the heated cushion (1).

Figure 13:
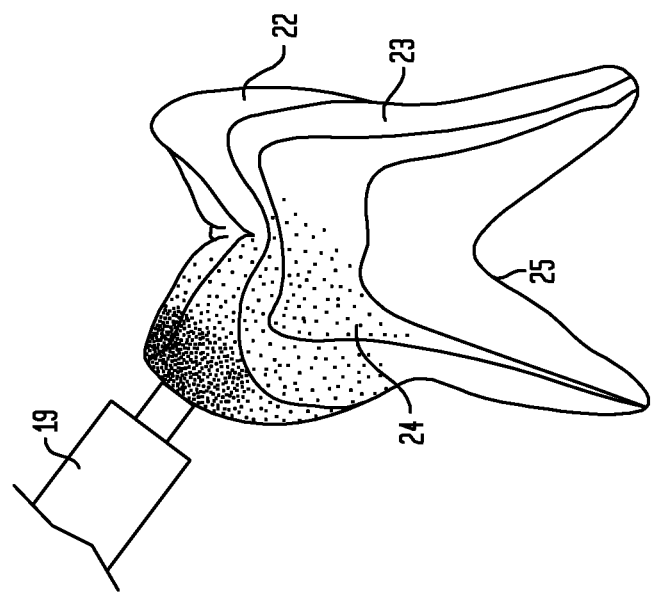
FIG. 13 illustrates the excess heat (shaded area) generated on the surface enamel layer (22), dentin layer (23), and the pulp tissue (24) of the tooth (25).

FIG. 13 shows the excess heat (shaded area) generated on the surface enamel layer (22), dentin layer (23), and the pulp tissue (24) of the tooth (25) from a point source (19) to obtain sufficient heat, spreading in a radial fashion, for a legitimate test of heat sensitivity in the pulp tissue (24).

Figure 14:
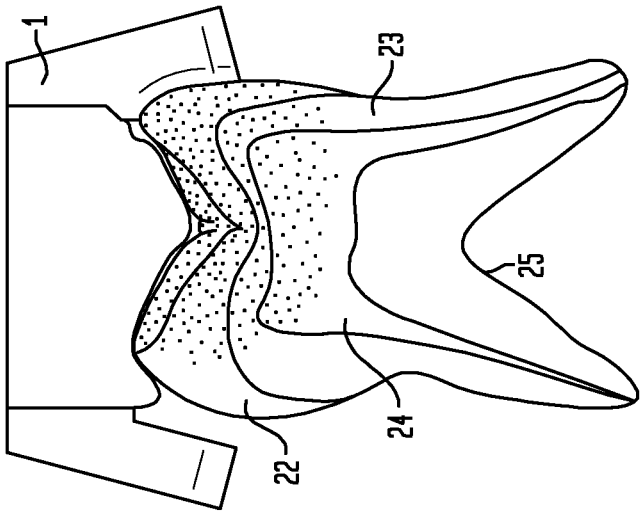
FIG. 14 illustrates the heat (shaded area) generated by a heated cushion (1) of the present invention that will conform to the surface enamel layer (22) of the tooth (25).

FIG. 14 shows the advantage of heat (shaded area) generated by a heated cushion (1) that will conform to the surface enamel layer (22) of the tooth (25) and heat a much greater surface area; transferring heat energy in a uniform fashion that is limited to a level that does not damage the enamel layer (22), the dentin layer (23), or the pulp tissue (24).

Figure 15:
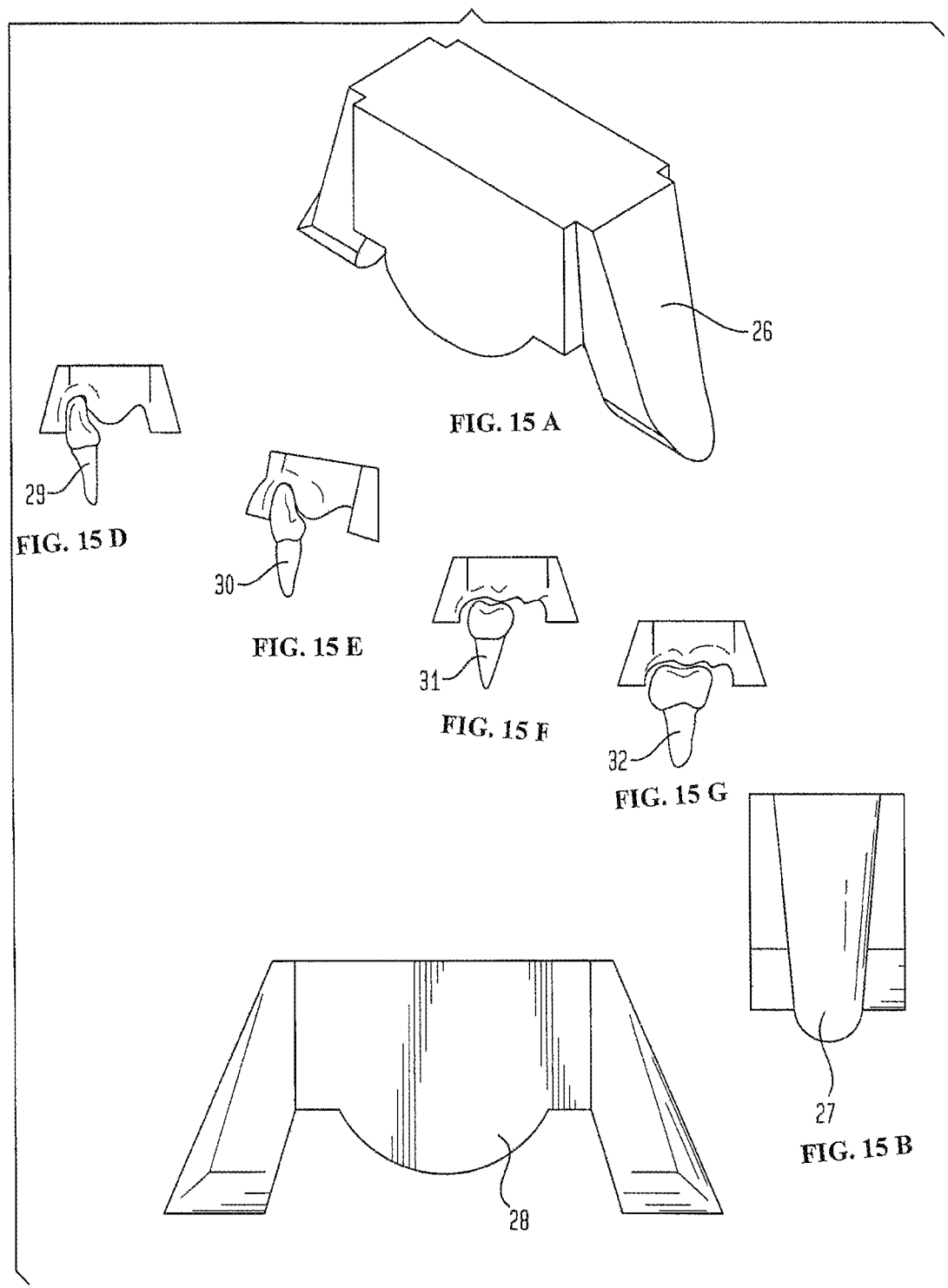
FIG. 15 A illustrates an oblique view (26) of a heated cushion without grooves and ridges.

FIG. 15 A shows an oblique view (26) of a heated cushion without grooves and ridges. An end view (27) (FIG. 15 B) of the same heated cushion and a side view (FIG. 15 C) of the same heated cushion (28), also illustrated is how the design of the heated cushion would allow it to relate to incisor teeth (29) (FIG. 15 D), canine teeth (30) (FIG. 15 E), bicuspid teeth (31) (FIG. 15 F), and molar teeth (32) (FIG. 15 G), producing a larger surface contact area as the teeth get larger.

FIG. 16 shows the testing device invention of the type that would have a docking station (33) (illustrated in cross section) which is connected by an electrical cord (34) to a household electrical outlet and has an on-off switch on the docking station (33) surface. The handle (11) of the testing device has contact rings (35) at the base which contact corresponding point contacts (36) in the docking station (33) that connect a circuit to charge the batteries in the handle (11). Contact rings (37) at the base of the handle (11) contact corresponding rings (38) in the docking station (33) to supply current to heat the heating element (15) in the heated cushion (1) in the tip for the testing device (2).

FIG. 17 shows the testing device invention resting in the docking station (33). The docking station has an on-off switch (39) on the surface and an electrical cord (34) which connects the docking station (33) to a household electrical outlet.

Figure 18:
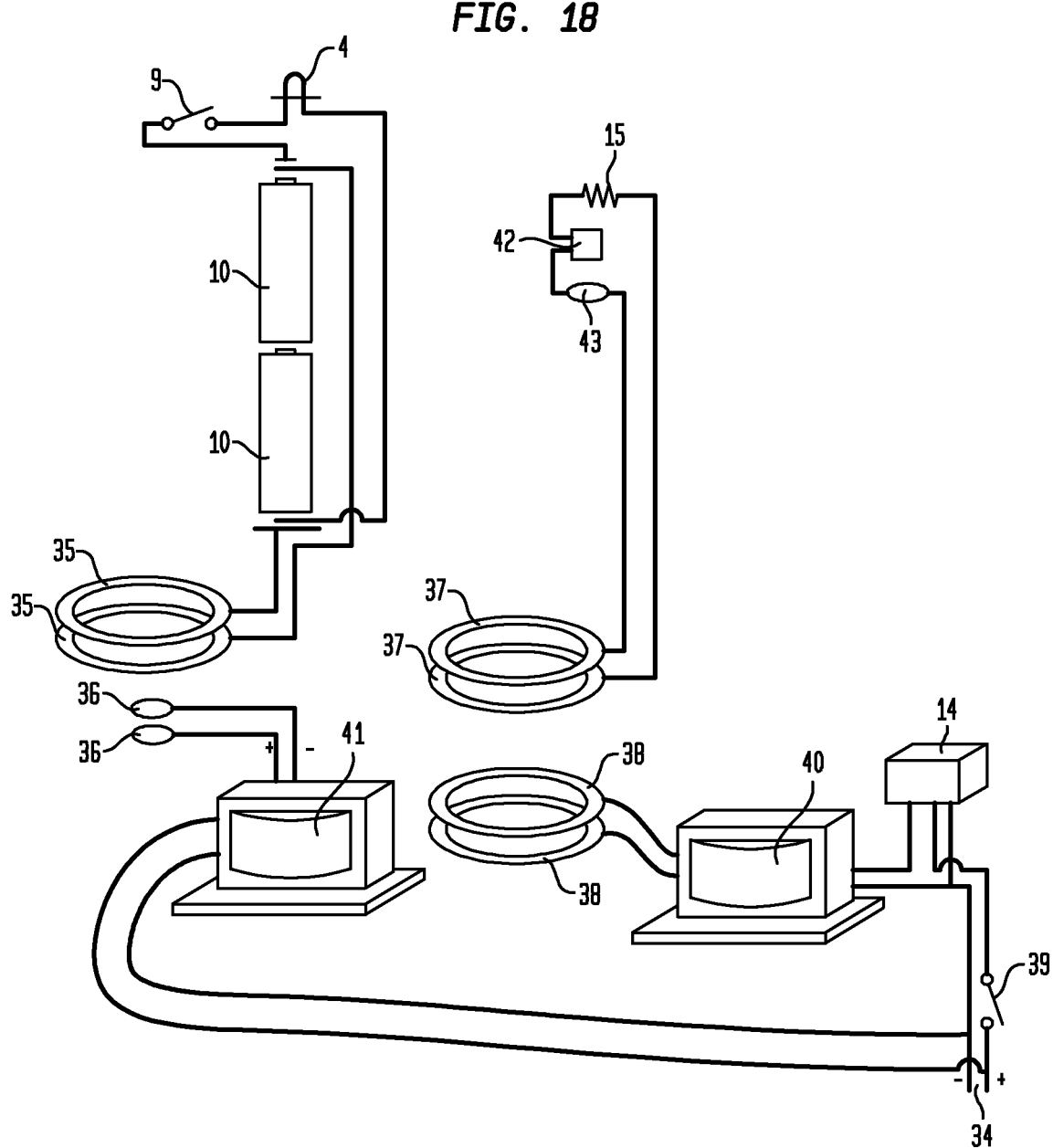
FIG. 18 illustrates the electrical circuitry for the testing device of the present invention utilizing a docking station (33).

FIG. 18 shows the electrical circuitry for a version of the testing device invention that utilizes a docking station (33). The electrical cord (34) intersects an on-off switch (39) which turns the heating element (15) circuitry on and off. A timing circuit (14) wired into the heating element (15) circuit is intended to turn the circuit off after a period of inactivity in the event the operator forgets to turn the testing device off. The heating element transformer (40) is wired to contact rings (38) that are in the docking station (33) in contact with contact rings (37) in the heating circuit in the testing device invention when the testing device invention is seated in the docking station (33). Contact rings (37) in the heating element (15) circuit provide electrical current to heat the heating element (15) which is wired in series with a metal thermostat switch (42) to maintain a temperature of around 140 Fahrenheit and a thermal fuse (43) as a safety device to prevent the heating element (15) from being overheated prior to testing. An additional degree of safety in using a docking station is when the testing device invention is separated from the docking station no additional increase in temperature in the related to the heating element (15) is possible because the current to the heating element (15) is interrupted. The recharging transformer (41) is wired into the circuitry preceding the on-off switch (39). The contact points (36) wired to the recharging transformer (41) are located in the docking station (33). The contact points (36) in the docking station (33) are in contact with contact rings (35) wired to the recharging circuit in the testing device invention when the testing device invention is seated in the docking station (33). A lighting circuit including batteries (10), a switch (9), and a white LED light (4), incorporated into the recharging circuit, allows for a viewing light in shaded areas of the mouth.

The foregoing description illustrates and describes embodiments of the invention. Additionally, the disclosure shows and describes only the preferred embodiments of the invention, but as mentioned above, it is to be understood that the invention is capable of use in various other combinations, modifications, and environments and is capable of changes or modifications within the scope of the inventive concept as expressed herein, commensurate with the above teachings and/or skill or knowledge of the relevant art. The embodiments described hereinabove are further intended to explain best modes known of practicing the invention and to enable others skilled in the art to utilize the invention in such or other embodiments and with the various modifications required by the particular applications or uses of the invention. Accordingly, the description is not intended to limit the invention to the form or application disclosed herein. Also, it is intended that the appended claims be construed to include alternative embodiments.

What is claimed is:

1. A device for testing a heat sensitivity in teeth comprising:
   a base; and
   a testing tip having a cushion,
   wherein the cushion comprises a heating element; and
   wherein the cushion is conformable to a contour of a tooth to be tested for a heat sensitivity and is conformable to contours of the shape of different types of teeth and wherein the cushion has a left side and a right side that are mirror images of each other that is configured for testing of all upper and lower teeth individually; and
   being capable of transferring heat energy from the cushion to the top surface and at least one side surface of the tooth tested for heat sensitivity.

2. The device according to claim 1, wherein said heating element is embedded in said cushion.

3. The device according to claim 1, being capable of transferring heat energy from the cushion whereby heat energy is dissipated in the cushion, minimizing transferring said heat energy.

4. The device according to claim 1, wherein the cushion is capable of generating heat on an enamel layer, dentin layer, and pulp tissue of the tooth without damaging the enamel layer, dentin layer, and pulp tissue with excessive heat energy.

5. The device according to claim 1, wherein the cushion is capable of spreading the heat in a radial fashion for identifying heat sensitivity in the pulp tissue.

6. The device according to claim 1, wherein the cushion is constructed of rubber material.

7. The device according to claim 6, wherein the cushion contains grooves and rubber between the grooves in the cushion is deformable and conformable to contours to the tooth.

8. The device according to claim 1, wherein the tip having the cushion is removable.

9. The device according to claim 1, wherein said different types of teeth include incisors, canines, premolars and molars.

10. The device according to claim 1, which further comprises a heat sensor and also a handle comprising circuitry, and wherein said heat sensor and said heating element are connected by circuitry in said handle to regulate a maximum temperature and a length of time of testing when activating said cushion.

11. The device according to claim 1, wherein said tooth has vertical sides and said cushion further comprises extensions capable of transferring heat and is for contacting and transferring heat to the vertical sides of said tooth to prevent injury to the pulp tissue of the tooth being tested.

12. The device according to claim 1, wherein said cushion extends down a vertical side of said tooth with minimal or no contact with tissue and has a depth limited to or less that of the vertical side and that limits the coverage to a single tooth with minimal or no contact with adjacent teeth.

13. The device according to claim 1, wherein said cushion further comprises the capability of transferring heat energy from the cushion to two side surfaces of the tooth.

14. The device according to claim 1, which further comprises a thermistor.

15. The device according to claim 1, wherein the cushion is constructed of silicon rubber material.

16. A method for testing a tooth for heat sensitivity comprising:
    applying a dental testing device comprising a testing tip having a cushion to a tooth;
    wherein the cushion comprises a heating element;
    heating the cushion with said heating element; and
    transferring heat energy from the cushion to the top surface and at least one side surface of the tooth,
    wherein the cushion conforms to a contour of the tooth and is conformable to contours of the shape of different types of teeth and wherein the cushion has a left side and a right side that are mirror images of each other.

17. The method according to claim 16, wherein said heating element is embedded in said cushion.

18. The method according to claim 16, which further comprises dissipating heat energy in the cushion, thereby minimizing said heat transfer from the cushion to adjacent teeth.

19. The method according to claim 16, which further comprises generating heat from the cushion wherein the level of heat on an enamel layer, dentin layer, and pulp tissue of the tooth is limited in order not to damage the tooth being tested.

20. The method according to claim 16, which further comprises spreading the heat from the cushion in a radial fashion for identifying heat sensitivity in the pulp tissue.

21. The method according to claim 16, wherein said different types of teeth include incisors, canines, premolars and molars.

22. The method according to claim 16, wherein said device comprises a heat sensor and also a handle comprising circuitry, and which further comprises connecting said heat sensor and said heating element by circuitry in said handle to regulate a maximum temperature and a length of time of testing when activating said heating element.

23. The method according to claim 22, which further comprises removing said cushion from the tip of the handle after said testing.

24. The method according to claim 16, wherein said cushion further comprises extensions and wherein said method further comprises contacting and transferring heat to vertical sides of said tooth from said extensions.

25. The method according to claim 16, which further comprises extending said cushion down a vertical side of said tooth with minimal or no contact with tissue and limiting a depth to that of the vertical side or less so that the coverage to a single tooth is with minimal or no contact with adjacent teeth.

26. The method according to claim 16, which comprises transferring heat energy from the cushion to two side surfaces of the tooth.

* * * * *